United States Patent [19]

Maier

[11] Patent Number: 5,243,995
[45] Date of Patent: Sep. 14, 1993

[54] GUIDE PROBE AND CLAMPING BUSHING FOR ECG CONTROLLED POSITIONING

[75] Inventor: Hans O. Maier, Lohfelden, Fed. Rep. of Germany

[73] Assignee: B. Braun Melsungen AG, Melsungen, Fed. Rep. of Germany

[21] Appl. No.: 791,880

[22] Filed: Nov. 13, 1991

[30] Foreign Application Priority Data

Nov. 21, 1990 [DE] Fed. Rep. of Germany ... 9015857[U]

[51] Int. Cl.$^5$ ............................................. A61B 5/00
[52] U.S. Cl. .................................... 128/772; 128/696; 604/283
[58] Field of Search ............... 128/657, 772, 639, 642, 128/786, 785, 784, 696; 604/164, 158, 95, 280, 283; 606/129

[56] References Cited

U.S. PATENT DOCUMENTS

| | | | |
|---|---|---|---|
| 3,087,486 | 4/1963 | Kilpatrick | 128/642 |
| 4,103,690 | 8/1978 | Harris | 606/129 |
| 4,471,777 | 9/1984 | McCorkle, Jr. | 606/129 |
| 4,552,127 | 11/1985 | Schiff | 606/129 |
| 4,860,757 | 8/1989 | Lynch et al. | 128/657 |
| 4,917,094 | 4/1990 | Lynch et al. | 128/657 |

*Primary Examiner*—Max Hindenburg
*Assistant Examiner*—Guy V. Tucker
*Attorney, Agent, or Firm*—Spensley Horn Jubas & Lubitz

[57] ABSTRACT

A guide probe includes an electrically conductive wire having a straight, projection-free distal end over which a flexible catheter may be advanced into the vena cava. An electric contact element is provided with a clamping bushing that is clampingly set onto the distal end of the wire. The clamping bushing is provided with a connection piece for an ECG lead. This enables a safe positioning and positional adjustment of the guide probe under ECG control.

5 Claims, 1 Drawing Sheet

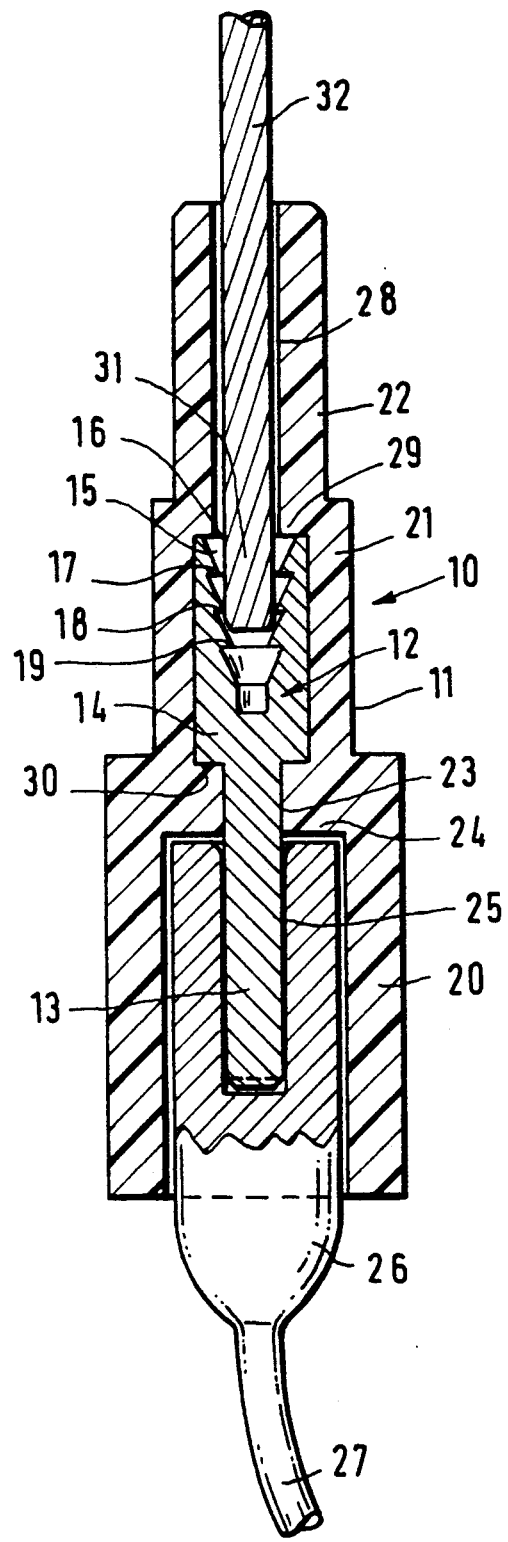

GUIDE PROBE AND CLAMPING BUSHING FOR ECG CONTROLLED POSITIONING

BACKGROUND OF THE INVENTION

1. Field of the Invention

The present invention relates to a guide probe, and in particular to a guide probe including an electrically conductive wire having a straight, projection-less distal end over which a flexible catheter may be advanced into the vena cava.

2. Description of Related Art

It is the purpose of such a guide probe to facilitate the placing of catheters by being introduced into the lumen of a vessel through a puncturing cannula after a puncture has been made by the puncturing cannula, the catheter being subsequently advanced to the desired position over the guide probe with the guide probe acting as a "pathfinder". This method of placing a catheter is called the "Seldinger technique". Up to the present, such guide probes have been introduced under fluoroscopic control.

To overcome obstacles in the advancement path of the guide probe, the tip of the guide probe is typically very flexible and is preferably provided with a semi-circular curvature. The remaining length of the wire, which can be up to 100 cm long, may be modified in various ways in order to obtain different degrees of flexibility for different purposes. For instance, the wire may be constructed as a strand of individual wires twisted about each other (European Patent 132 694). It is also known to combine flexible twisted sections alternatingly with rigid sections of solid material to form a wire (German Utility Model 86 08 051) or to subdivide an integral wire core into sections of different rigidity by providing partial constrictions in the cross section (German Utility Model 89 00 077).

Regardless of the structure of the wire, the distal end of the wire is always straight, projection-less, and is free of any protrusions, so that the catheter may be threaded onto the guide probe from its distal end after the guide probe has been placed. The requirement of keeping the distal end of the wire free has made it necessary, up to the present, to perform the positioning under fluoroscopic X-ray control and to also use the X-ray picture for positional adjustment. This constitutes a major difference with respect to catheter sets in which a guide rod is inserted into the catheter during manufacture, acting as a stylet filling the lumen in order to be introduced into the blood vessel together with the catheter. The catheter is connected to the stylet by coupling members at their respective distal ends, which coupling members allow for a ready connection of a lead to an ECG apparatus in order to draw conclusions on the position of the tip of the catheter from the ECG paths, thereby avoiding the detrimental radiation exposure involved with X-ray control (German Utility Model 85 09 649).

It is an object of the present invention to make the placing and the positioning adjustment of guide probes possible under ECG control.

SUMMARY OF THE INVENTION

In accordance with the present invention, this and other objectives are achieved by providing an electric contact element having a clamping bushing that may be clampingly set onto the distal end of the wire. The clamping bushing is provided with a connection piece for an ECG lead.

The guide probe of the present invention may be used in accordance with the following technique. First, a vessel is punctured using a puncture cannula. The guide probe is then advanced into the vena cava through the puncture cannula. The puncture cannula is withdrawn over the distal end of the guide probe. The electric contact element of the present invention is then applied to the distal end of the guide probe. An intracardiac ECG is lead via the ECG lead connected to the connection piece of the present invention. The ECG enables the user to draw conclusions regarding the position of the tip of the guide probe and thereby correctly position the tip of the guide probe. After the tip of the guide probe has been correctly positioned, the contact element is removed from the distal end of the guide probe and the catheter is advanced up to the desired location via the guide probe "pathfinder". Since the tip of the catheter follows the correctly positioned guide probe, false positioning of the catheter is reduced or eliminated.

According to another technique, the electric contact element may be slipped onto the wire of the guide probe after the puncture cannula has been withdrawn and after the catheter has already been pushed onto the guide probe. The ECG lead starts only when the catheter tip reaches the vicinity of the tip of the guide probe that advances towards the desired location. As soon as the ECG graph indicates the correct placement of the catheter tip, the guide probe is removed from the catheter and an infusion hose or the like may be connected to the catheter hub in the usual manner.

The placing of a catheter according to the Seldinger technique is particularly preferable when there are obstacles to be overcome in the lumen of a vessel. In accordance with the present invention, the placing of a catheter according to the Seldinger technique becomes safer for a patient since the radiation exposure by X-ray photography is eliminated. Moreover, the elimination of X-ray photography saves costs. Further, the handling of the guide probe and the catheter is made easier for a user since the user is no longer required to sharply watch an X-ray picture but need only respond to ECG graph signals instead.

In a preferred embodiment of the invention the clamping bushing has a conical cavity with an insertion opening for the wire end. Opposite the insertion opening, the clamping bushing is provided with the connection piece. The cavity tapers towards the connection piece and has a pine-tree profile on its inner surface. Thus, a compact structure of the clamping bushing and its adaptation to wires of different diameters is achieved. Each tier of the pine-tree profile of the inner surface effects a clamping hold in the clamping bushing for the associated wire diameter.

Preferably, the clamping bushing is formed integrally with the connection piece in the form of a pin. The clamping bushing is preferably made of metal and is preferably accommodated in a tubular housing of plastic material. One end of the housing may be provided with a sleeve extension. The peripheral wall of the sleeve extension surrounds the connection piece and is in spaced relationship with the connection piece. Thus, both the clamping bushing and the connection piece are shielded from the outside and the sleeve extension, with the connection piece provided centrally therein, forms a plug into which an electric coupling of an ECG lead leading to an ECG apparatus may be pushed.

At the end of the housing opposite the insertion opening of the cavity, a socket with a straight channel for guiding the end of the wire may be provided. The socket facilitates the controlled insertion of the wire end into the insertion opening of the clamping bushing. The socket also serves to stabilize the plug-in connection for ensuring reliable ECG signals. Further, the socket piece gives the housing a handy length that makes it easier to hold when assembling the parts, which is particularly important because the guide probe protruding into the vessel is meant to be left as stationary as possible.

BRIEF DESCRIPTION OF THE DRAWINGS

A detailed description of a preferred embodiment of the invention will be made with reference to the accompanying drawing.

FIG. 1 shows a longitudinal section of an electric contact element in use.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

As shown in FIG. 1, an electric contact element 10 substantially comprises a tubular housing 11 of electrically non-conductive plastic material including a metal clamping bushing 12. The clamping bushing 12 has a circular cylindrical elongate body 14 that has a coaxial conic cavity 15 along the greater part of its length. The coaxial conic cavity 15 is accessible through an insertion opening 16 in one end face of the body 14 and is closed at the other end.

A connection piece 13 for an ECG lead 27 extends vertically from the end surface of the body 14 opposite the insertion opening 16. The connection piece 13 is designed as a circular cylindrical contact pin. The axis of the connection piece 13 lies along the central axis of the cavity 15.

The oblique closed inner surface of the conic cavity 15 has a pine-tree profile. This results in axially successive sharp-edged rings 17, 18, 19, defining circular passages of different diameters. Since the cavity 15 tapers from the insertion opening 16 towards the connection piece 13, the passage of the ring 17 is the largest and the passage of the ring 19 is the smallest.

The one-piece tubular housing 11 comprises three coaxially successive sections 20, 21, 22, which are of circular cylindrical design, respectively. The section 21 is arranged between the sections 20 and 22 and forms a circular cylindrical chamber in which the body 14 of the clamping bushing 12 is fittingly accommodated so that the clamping bushing 12 is snug within the housing 11. The connection piece 13, integrally formed with the body 14, extends through a bore 23 in a transversal wall 24 of the housing 11 and terminates freely in the circular cylindrical inner space 25 of a sleeve extension constituting the section 20. The inner surface of the sleeve extension 20 may be plane or threaded. The end of the connection piece 13 is set back inwardly with respect to the opening of the sleeve extension 20. The connection piece 13 and the sleeve extension 20 form a plug bushing into which a coupling member 26 of the ECG lead 27 may be plugged.

The other section 22 of the housing 11 is formed as a socket with a straight channel 28. The channel 28 is open at both ends and opens into the inside of the insertion opening 16 of the cavity 15 of the clamping bushing 12. An annular shoulder 29 is provided at the opening of the channel 28 into the cavity 15. The annular shoulder 29 is arranged opposite a parallel annular shoulder 30 at the opening of the bore 23 into the cavity 15. Both of the annular shoulders 29 and 30 abut the end faces of the body 14 of the clamping bushing 12 and hold the clamping bushing fixed.

The straight, projection-free distal end 31 of the electrically conductive wire 32 of the guide probe is advanced through the channel 28 of the socket section 22 into the cavity 15 of the clamping bushing 12 (the other end of the electrically conductive wire 32 is inserted into a vena cava). Depending on the diameter of the wire 32, the distal end 31 of the wire will get stuck in one of the rings 17, 18 or 19 and will be clampingly held by the sharp inner edges thereof. Thus, an electrical connection between the wire 32 and the ECG lead 27 will be established. Electrical heart pulses will be supplied through the wire 32 directly from the tip of the wire to an ECG apparatus connected to the lead 27. The position of the wire tip may be read from the ECG graphs on a monitor and may be adjusted if need be.

The presently disclosed embodiment is to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A guide probe, comprising:
    an electrically conductive wire having a substantially straight, projection-free distal end, the distal end of the wire being configured such that a flexible catheter is advanceable over the distal end of the wire,
    an electric contact element having a clamping bushing including a coaxial cavity for clampingly engaging the distal end of the wire within said cavity,
    a connection piece associated with the clamping bushing for connecting the clamping bushing and an ECG lead,
    whereby the wire is positionable under ECG control and the contact element is removable from the distal end to thereby permit the advancement of a flexible catheter over the distal end of the wire.

2. A guide probe, comprising:
    an electrically conductive wire having a substantially straight, projection-free distal end,
    an electric contact element having a clamping bushing for clampingly engaging the distal end of the wire,
    a connection piece associated with the clamping bushing for connecting the clamping bushing and an ECG lead, whereby the wire is positionable under ECG control, wherein
    the clamping bushing defines a substantially conic cavity having an insertion opening for the distal end of the wire,
    the connection piece and the insertion opening are positioned on substantially opposite ends of the clamping bushing, and the substantially conic cavity tapers towards the connection piece and defines an inner surface having a plurality of axially successive sharp-edged rings, the plurality of rings defining a plurality of circular passages of differing diameters.

3. A guide probe, comprising:

an electrically conductive wire having a substantially straight, projection-free distal end, an electric contact element having a clamping bushing for clampingly engaging the distal end of the wire, a connection piece associated with the clamping bushing for connecting the clamping bushing and an ECG lead, whereby the wire is positionable under ECG control, wherein the clamping bushing and the connection piece comprise an integrally formed metal pin and further comprising:

a substantially tubular plastic housing for accommodating the clamping bushing and the connection piece, a sleeve extension having a peripheral wall provided at one end of the housing, the peripheral wall of the sleeve extension surrounding the connection piece and being in spaced relationship with the connection piece.

4. The guide probe as defined in claim 3, comprising:

a socket provided at an end of the housing adjacent the insertion opening of the cavity, the socket defining a substantially straight channel for guiding the distal end of the wire.

5. A method for positioning a guide probe under ECG control, comprising:

puncturing a vessel using a puncture cannula, advancing the guide probe into a vena cava through the puncture cannula, the guide probe comprising an electrically conductive wire having a substantially straight, projection-free distal end, withdrawing the puncture cannula over the distal end of the wire, clampingly engaging the distal end of the wire using an electric contact element having a clamping bushing, connecting the clamping bushing and an ECG lead using a connection piece associated with the clamping bushing, and positioning the wire under ECG control.

* * * * *